United States Patent [19]

Johncock et al.

[11] Patent Number: 5,710,242
[45] Date of Patent: Jan. 20, 1998

[54] HIGH TEMPERATURE EPOXY RESINS FROM HYDROGENATED QUINOXALINES

[75] Inventors: Peter Johncock, Farnborough; David Alan Jones, Malvern, both of Great Britain

[73] Assignee: The Secretary of State for Defence in her Britannic Majesty's Government of the United Kingdom of Great Britain and Northern Ireland of Defence Evaluation Research Agency, United Kingdom

[21] Appl. No.: 700,371

[22] PCT Filed: Feb. 16, 1995

[86] PCT No.: PCT/GB93/00326

§ 371 Date: Oct. 25, 1996

§ 102(e) Date: Oct. 25, 1996

[87] PCT Pub. No.: WO95/23142

PCT Pub. Date: Aug. 31, 1995

[30] Foreign Application Priority Data

Feb. 24, 1994 [GB] United Kingdom ............... 9403563

[51] Int. Cl.[6] ............ C07D 405/14; C08G 59/32; C08G 59/26
[52] U.S. Cl. ............ 528/407; 528/406; 540/473; 540/573; 544/235; 544/336; 544/349; 544/350; 544/353; 544/357
[58] Field of Search ............... 544/235, 336, 544/349, 350, 353, 357; 528/406, 407; 540/473, 573

[56] References Cited

U.S. PATENT DOCUMENTS

| | | | |
|---|---|---|---|
| 2,951,822 | 2/1960 | Reinking | 549/552 |
| 3,429,833 | 2/1969 | Porret | 528/96 |
| 3,828,066 | 8/1974 | Porret | 528/96 |

Primary Examiner—Frederick Krass
Attorney, Agent, or Firm—Nixon & Vanderhye

[57] ABSTRACT

A multi-functional epoxy resin with good high temperature properties allowing prolonged service at temperatures above 120° C. is derived from a precursor of formula (I):

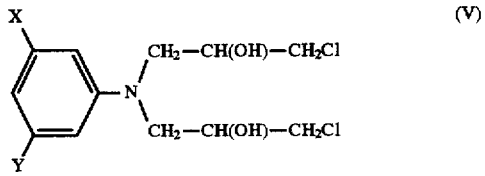

(V)

in which $R^3$ to $R^8$ inclusive are independently selected from hydrogen, $C_1$ to $C_3$ alkyl or halo-alkyl and $R^9$ is hydrogen, alkyl or halogen, and in which n has the value 0, 1 or 2. The precursor (I) may be self-coupled or cross-coupled with precursors of other epoxy compounds of the TGDDM type. Such cross-coupling gives rise to a complex mixture containing not only the mixed product, but also the self-coupled products of each constituent. Regardless of the precise chemical make-up of the mixture, the observed glass transition temperature is higher than for TGDDM resins formed without precursor (I). If the substituent at the $R^9$ position is alkyl or halogen, oligomer formation is suppressed and a less complex mixture results.

15 Claims, No Drawings

HIGH TEMPERATURE EPOXY RESINS FROM HYDROGENATED QUINOXALINES

This is a 35 USC 371 of PCT/GB95/00326 filed Feb. 16, 1995.

The present invention relates to epoxy resins and in particular to epoxy resins for use in fibre-reinforced composite materials suitable for aerospace applications where high temperatures may be encountered, for example due to aerodynamic heating and proximity to engines and exhaust gases.

Currently, the most widely-used high performance carbon fibre composite materials are based on the tetrafunctional N-glycidyl epoxy system, bis[N,N-bis(2,3-epoxypropyl)-4-aminophenyl]methane (TGDDM). One of the drawbacks of N,N-diglycidyl epoxy system, of which TGDDM is an example, is that they display reduced functionality in their reactions with amine hardeners because of intramolecular cyclisation reactions which compete with the desired cross-linking processes. This has the effect of reducing the glass transition temperature, $T_g$, because it effectively preserves polymer mobility within the structure due to the reduction in the number of cross-links.

Whilst it is recognised that TGDDM resins have a dry $T_g$ value of around 260° to 265° C., in practice their use is limited to applications requiring a maximum service temperature of around 125° C. This is because they have a tendency to pick up moisture from the atmosphere. Absorbed water has a plasticising effect on such resins, reducing the $T_g$ and hence limiting the maximum service temperature.

Attempts have been made to exploit commercially epoxy resins with a higher $T_g$ or reduced water affinity, thus providing a higher maximum service temperature, but none has shown an improvement over TGDDM in overall performance It is therefore an object of the present invention to provide an epoxy resin system which overcomes some of the disadvantages displayed in prior art systems, with particular emphasis on eliminating intramolecular cyclisation and providing good resistance to oxidative aging.

It is a further object of the invention to provide a method of increasing the effective functionality of commercially-available materials and thereby increase their glass transition temperatures through enhanced cross-link density.

According to the invention there is provided a multi-functional epoxy resin derived from a precursor of formula (I):

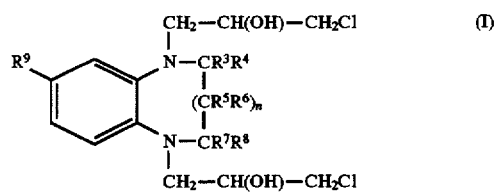

wherein $R^3$ to $R^8$ inclusive are independently selected from hydrogen, $C_1$ to $C_3$ alkyl or halo-alkyl, and wherein n=0, 1 or 2, and wherein $R^9$=hydrogen, alkyl or halogen.

In one aspect of the invention, the precursor (I) is substituted at the $R^9$ position with hydrogen and self-coupled under acidic conditions in the presence of formaldehyde or benzaldehyde to give, after subsequent dehydrochlorination, a multi-functional compound of formula (II):

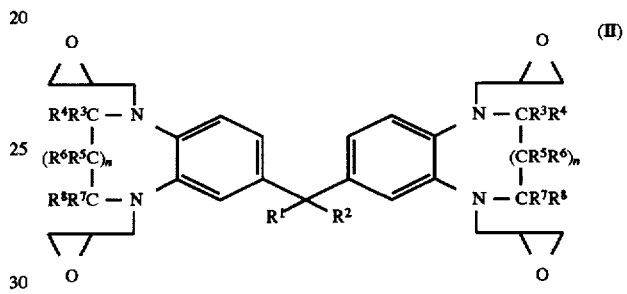

and higher oligomers (III), wherein $R^3$ to $R^8$ inclusive are independently selected from hydrogen, $C_1$ to $C_3$ alkyl, halo-alkyl, or optionally-substituted aryl, and wherein n=0,1 or 2, and x=0 to 10

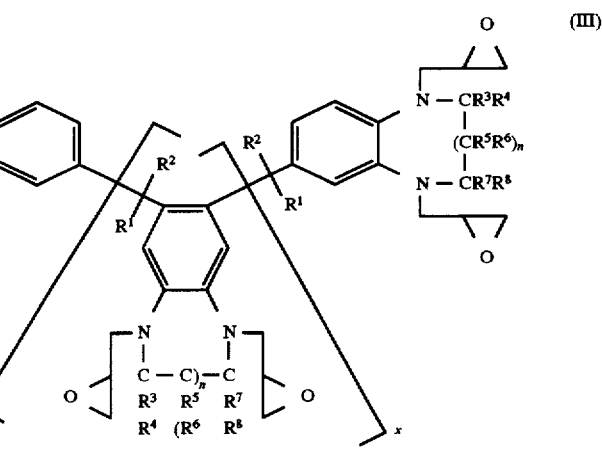

In another aspect of the invention, the precursor (I) is substituted at the $R^9$ position with alkyl or halogen and self-coupled in the presence of formaldehyde or benzaldehyde to give, after subsequent dehydrochlorination, a multi-functional compound of formula (IV):

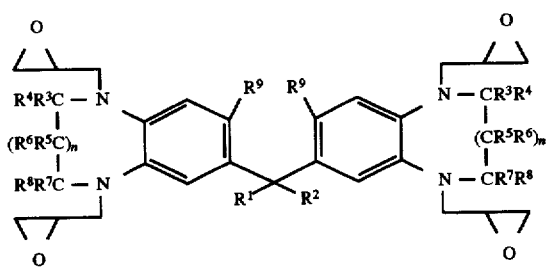

wherein $R^3$ to $R^8$ inclusive are independently selected from hydrogen, $C_1$ to $C_3$ alkyl, halo-alkyl, or optionally-substituted aryl, and wherein n=0, 1 or 2.

The multi-functional compound (IV) is a substituted version of compound (II) in which the formation of higher oligomers (III) is prevented by the substituents $R^9$.

In the above-mentioned self-coupling reactions, when formaldehyde is used as the coupling reagent, $R^1$ and $R^2$ are both hydrogen. If benzaldehyde is used, $R^1$ is $C_6H_5$ and $R^2$ is hydrogen.

Preferably, the heterocycles are six-membered rings and the substituents are all hydrogen, so that, in the above formulae, $R^1$ to $R^8$ inclusive are hydrogen and n=0.

In another preferred form of the invention, $R^1$ is $C_6H_5$, all other optional constituents being hydrogen.

Seven- and eight-membered nitrogen heterocycles may also be prepared, when n=1 or n=2, respectively. These larger ring sizes are more difficult to synthesise and the higher aliphatic content results in a reduction in $T_g$, but useful properties are nevertheless obtained.

Alternatively, the precursor (I) in which $R^9$ is hydrogen may be cross-coupled with further precursor (I) in which $R^9$ is alkyl or halogen to give a product in which the degree of oligomerisation is controlled by variation of the relative proportions of the precursor variants.

Alternatively, the material (I) may be cross-coupled with the precursors of other epoxy compounds of the TGDDM type, including halogenated derivatives covered by European Patent EP 0 076 584 B. One particularly preferred cross-coupled material involves the reaction between precursor (I) of the present invention and precursor (V) depicted below:

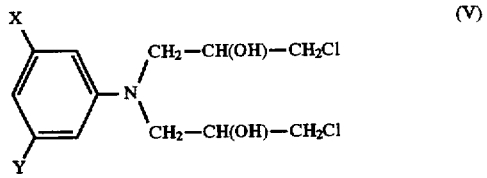

in which X and/or Y are halogen, haloaklyl or hydrogen.

In practice, such cross-coupling gives rise to a complex mixture containing not only the mixed product (VI, see below), but also the self-coupled products (II) and (VII) of each constituent. Regardless of the precise chemical make-up of such a mixture, the observed $T_g$ is higher than for the unmodified resin.

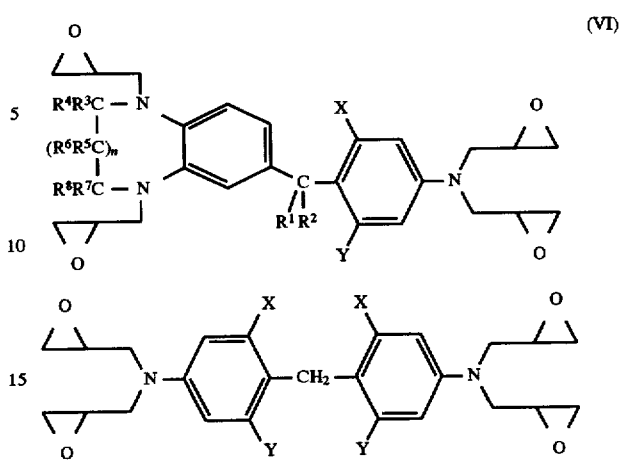

Epoxy compounds of the present invention may be cured to form high molecular weight polymers by conventional techniques using known curing agents such as diamino-diphenylsulphone (DDS), bis(4-aminophenyl)methane (DDM) or 1,3-diaminobenzene. An epoxy compound according to the present invention may be cured on its own or combined in a mixture of other epoxy compounds and then cured. Such a mixture may include one or more epoxy compounds according to the present invention, and one or more known epoxy compounds. Any such mixture may be tailored to the requirements of the end use to which the cured material is to be applied.

Reinforced composite materials may be made with suitable reinforcing materials by known techniques, using the epoxy compounds of the invention in any of the above combinations to form the polymer matrix.

Embodiments of the invention will now be described by way of example.

EXAMPLE 1

TGQF (II, n=0, $R^1$ to $R^8$=H)

Quinoxaline was hydrogenated at 60 psi, 50° C. with $PtO_2$ catalyst in ethanol to produce 1,2,3,4-terahydroquinoxaline (THQ).

13.4 g (0.1 mol) of THQ, 37 g (0.4 mol) epichlorohydrin, 30 cm³ of benzene and 0.27 cm³ (0.0045 mol) of acetic acid were reacted under nitrogen at 60° C. until the reaction was shown to be complete by reverse phase HPLC (approximately 3 hours). Solvent and excess reactants were removed by distillation. 30 cm³ water and 15 g concentrated HCl were added under nitrogen and stirred to dissolve at 60° C., then 5.7 g (approximately 0.07 mol) 37% aqueous formaldehyde was added and the mixture stirred for 3 hours at 60° C. After cooling, the solution was neutralised with 10% aqueous NaOH, upon which it separated into an organic and an aqueous layer. The aqueous layer was decanted off and the organic layer dried thoroughly under vacuum. The resulting friable foamed solid was powdered finely, 10.8 g (0.27 mol) powdered NaOH and 120 cm³ butanone were added under nitrogen, and the resulting slurry was stirred vigorously for 2 hours at 60° C. The reaction mixture was allowed to cool and settle, was filtered, and the solvent removed from the filtrate to give an amber coloured resinous product. This was purified by precipitation and dried thoroughly, giving a solid product in typically 75% yield.

EXAMPLE 2

TGBDZF (II, n=1, $R^1$ to $R^8$=H)

o-phenylene diamine was purified by sublimation. The purified o-phenylene diamine and acrylic acid were reacted according to the method reported by Bachman and Heisey in JACS 71 (1949) p1986, to produce 2-oxo-1,3,4,5-tetrahydro-1,5-benzodiazepine. Using glassware which had been thoroughly dried, 4.0 g (0.025 mol) of this amide and 40 cm$^3$ of toluene were heated to 95° C. under nitrogen and 20 cm$^3$ "Redal" (70% sodium bis(2-methoxyethoxy) dihydroaluminate in toluene) was added dropwise over 1 hour with stirring. HPLC showed the absence of the amide. A further 20 cm$^3$ of toluene was added to reduce the amide. A further 20 cm$^3$ of toluene was added to reduce the viscosity, followed by the dropwise addition of 20 cm$^3$ water with stirring. The organic layer was decanted off, filtered under nitrogen and the solvent removed by rotary evaporation. Recrystallisation from benzene gave the required diamine.

1.48 g (0.01 mol) of this diamine, 3.7 g (0.04 mol) of epichlorohydrin, 3 cm$^3$ of benzene and 0.027 cm$^3$ (0.00045 mol) of acetic acid were reacted under nitrogen at 60° C. until reaction was shown to be complete by reverse phase HPLC (approximately 3 hours). Solvent and excess reactants were removed by distillation. 3.0 cm$^3$ of water and 3.0 g of concentrated HCl were added under nitrogen and stirred to dissolve at 60° C., then 0.57 g (approximately 0.007 mol) of 37% aqueous formaldehyde was added and the mixture stirred for 10 hours at 90° C. After cooling, the solution was neutralised with 10% aqueous NaOH, upon which it separated into an organic and an aqueous layer. The aqueous layer was decanted off and the organic layer dried thoroughly under vacuum. The resulting friable foamed solid was powdered finely, 1.0 g (0.025 mol) powdered NaOH and 12 cm$^3$ butanone were added under nitrogen, and the resulting slurry was stirred vigorously for 2 hours at 60° C. The reaction mixture was allowed to cool and settle, was filtered, and the solvent removed from the filtrate to give an amber coloured resinous product. This was purified by precipitation and dried thoroughly, giving a solid product.

EXAMPLE 3

TGQB (II, n=0, $R^1$=$C_6H_5$, $R^2$ to $R^8$=H)

Quinoxaline was hydrogenated at 60 psi, 50° C. with PtO$_2$ catalyst in ethanol, to produce 1,2,3,4-tetrahydroquinoxaline (THQ).

1.34 g (0.01 mol) of THQ, 3.7 g (0.04 mol) epichlorohydrin, 3 cm$^3$ of benzene and 0.027 cm$^3$ (0.00045 mol) of acetic acid were reacted under nitrogen at 60° C. until the reaction was shown to be complete by reverse phase HPLC (approximately 3 hours). Solvent and excess reactants were removed by distillation. 3.0 cm$^3$ of water and 1.5 g of concentrated HCl were added under nitrogen and stirred to dissolve at 70° C., then 0.64 g (approximately 0.006 mol) of benzaldehyde was added and the mixture stirred for 4 hours at 90° C., during which time some organic material separated out. After cooling, the solution was neutralised with 10% aqueous NaOH, upon which it separated further into an organic and an aqueous layer. The aqueous layer was decanted off and the organic layer dried thoroughly under vacuum. The resulting friable foamed solid was powdered finely, 1.0 g (0.025 mol) powdered NaOH and 12 cm$^3$ butanone were added under nitrogen, and the resulting slurry stirred vigorously for 1 hour at 60° C. The reaction mixture was allowed to cool and settle, was filtered, and the solvent removed from the filtrate to give an amber coloured resinous product. This was purified by precipitation and dried thoroughly, giving a tacky solid product.

EXAMPLE 4

TGDMQF (II n=0, $R^1$=$R^2$=$R^3$=$R^7$=H, $R^4$=$R^5$=$CH_3$)

1,2,3,4-tetrahydro-2,3-dimethylquinoxaline was produced by the sodium reduction of an ethanol solution of 2,3-dimethylquinoxaline at 90° C. (Gibson, J Chem Soc (1927) p343). The product was purified by precipitation from HCl solution with NaOH. 1.62 g (0.01 mol) of tetrahydrodimethylquinoxaline, 3.7 g (0.04 mol) of epichlorohydrin, 3 cm$^3$ of benzene and 0.1 cm$^3$ (0.0017 mol) of acetic acid were reacted under nitrogen at 60° C. until the reaction was shown to be complete by reverse phase HPLC (approximately 4 hours). Solvent and excess reactants were removed by distillation. 3 cm$^3$ of water and 1.5 g of concentrated HCl were added under nitrogen and stirred to dissolve at 50° C., then 0.57 g (approximately 0.007 mol) 37% aqueous formaldehyde was added and the mixture stirred for 4 hours at 50° C. After cooling, the solution was neutralised with 10% aqueous NaOH, upon which it separated into an organic and an aqueous layer. The aqueous layer was decanted off and the organic layer dried thoroughly under vacuum. The resulting friable foamed solid was powdered finely, 1.0 g (0.025 mol) of powdered NaOH and 12 cm$^3$ of butanone were added under nitrogen, and the resulting slurry stirred vigorously for 1 hour at 60° C. The reaction mixture was allowed to cool and settle, was filtered, and the solvent removed from the filtrate to give an amber coloured resinous product. This was purified by precipitation and dried thoroughly, giving a solid product.

EXAMPLE 5

XC (VI, n=0, $R^1$ to $R^8$=H, X=Cl, Y=H)

Quinoxaline was hydrogenated at 60 psi, 50° C. with PtO$_2$ catalyst in ethanol, to produce 1,2,3,4-tetrahydroquinoxaline (THQ).

13.4 g (0.1 mol) of THQ, 37 g (0.4 mol) of epichlorohydrin, 30 cm$^3$ of benzene and 0.27 cm$^3$ (0.0045 mol) of acetic acid were reacted under nitrogen at 60° C. until the reaction was shown to be complete by reverse phase HPLC (approximately 3 hours). Solvent and excess reactants were removed by distillation.

To 12.8 g (0.1 mol) of 3-chloroaniline and 5.0 cm$^3$ of acetic acid under nitrogen at room temperature was added 37 g (0.4 mol) of epichlorohydrin. The mixture was heated gradually to 80° C., and stirred at this temperature until reverse phase HPLC showed reaction to be complete (approximately 4.5 hours). Excess reactants were removed by distillation.

0.05 mol of the dichlorohydrin of THQ plus 0.05 mol of the dichlorohydrin of 3-chloroaniline were dissolved in 30 cm$^3$ of water and 15.5 g of concentrated HCl at 75° C. under nitrogen. 4.9 g (approximately 0.6 mol) of 37% aqueous formaldehyde was added and the mixture stirred under nitrogen at 75° C. for 3 hours. After cooling, the solution was neutralised with 10% aqueous NaOH, upon which it separated into an organic and an aqueous layer. The aqueous layer was decanted off and the organic layer dried thoroughly under vacuum. The resulting friable foamed solid was powdered finely, 10.8 g (0.27 mol) of powdered NaOH and 120 cm$^3$ of butanone added under nitrogen, and the resulting slurry stirred vigorously for 40 minutes at 55° C. The reaction mixture was allowed to cool and settle, was filtered, and the solvent removed from the filtrate to give an amber coloured resinous product. This was purified by precipitation and dried thoroughly, giving a highly viscous product in typically 80% yield.

EXAMPLE 6

XCD (VI, n=0, $R^1$ to $R^8$=H, X=Y=Cl)

Quinoxaline was hydrogenated at 60 psi, 50° C. with $PtO_2$ catalyst in ethanol, to produce 1,2,3,4-tetrahydroquinoxaline (THQ).

13.4 g (0.1 mol) of THQ, 37 g (0.4 mol) of epichlorohydrin, 30 cm³ of benzene and 0.27 cm³ (0.0045 mol) of acetic acid were reacted under nitrogen at 60° C. until the reaction was shown to be complete by reverse phase HPLC (approximately 3 hours). Solvent and excess reactants were removed by distillation.

To 16.2 g (0.1 mol) of 3,5-dichloroaniline and 5.0 cm³ of acetic acid under nitrogen at room temperature was added 37 g (0.4 mol) of epichlorohydrin. The mixture was heated gradually to 80° C., and stirred at this temperature until reverse phase HPLC showed reaction to be complete (approximately 13 hours). Excess reactants were removed by distillation.

0.05 mol of the dichlorohydrin of THQ plus 0.05 mol of the dichlorohydrin of 3,5-dichloroaniline were dissolved in 30 cm³ of water, 15.5 g of concentrated HCl and 20 cm³ of dioxan at 75° C. under nitrogen. 4.9 g (approximately 0.6 mol) of 37% aqueous formaldehyde was added and the mixture was stirred under nitrogen at 80° C. for 4½ hours. After cooling, the solution was neutralised with 10% aqueous NaOH, upon which it separated into an organic and an aqueous layer. The aqueous layer was decanted off and the organic layer dried thoroughly under vacuum. The resulting friable foamed solid was powdered finely, 10.8 g (0.27 mol) of powdered NaOH and 120 cm³ of butanone added under nitrogen, and the resulting slurry stirred vigorously for 40 minutes at 55° C. The reaction mixture was allowed to cool and settle, was filtered, and the solvent removed from the filtrate to give an amber coloured resinous product. This was purified by precipitation and dried thoroughly, giving a highly viscous product in typically 80% yield.

EXAMPLE 7

(IV, n=0, $R^1$ to $R^8$=H, $R^9$=$CH_3$)

3,4-diaminotoluene was purified by sublimation. 12.2 g (0.1 mol) diaminotoluene was dissolved in 100 cm³ water at 70° C. To this was added 15.0 g 40% aqueous glyoxal solution (0.104 mol) in a solution of 21.5 g sodium bisulfite in 100 cm³ water. After 15 minutes at 60° C. the reaction mixture was cooled and 15 g potassium carbonate added. The product, 6-methylquinoxaline, was extracted with dichloromethane and purified by distillation. 6-methylquinoxaline was hydrogenated at 60 psi, 50° C. with $PtO_2$ catalyst in ethanol, to produce 1,2,3,4-tetrahydro-6-methylquinoxaline. 1.48 g (0.01 mol) 1,2,3,4-tetrahydro-6-methylquinoxaline, 3.7 g (0.04 mol) epichlorohydrin, 3 cm³ benzene and 0.027 cm³ (0.00045 mol) acetic acid were reacted under nitrogen at 60° C. until reaction was shown to be complete by reverse phase HPLC (approximately 3 hours). Solvent and excess reactants were removed by distillation. 3.0 cm³ of water and 1.5 g of concentrated HCl were added under nitrogen and stirred to dissolve at 60° C., then 0.49 g (approximately 0.006 mol) of 37% aqueous formaldehyde was added and the mixture stirred for 2 hours at 60° C. After cooling, the solution was neutralised with 10% aqueous NaOH, upon which it separated into an organic and an aqueous layer. The aqueous layer was decanted off and the organic layer dried thoroughly under vacuum. The resulting friable foamed solid was powdered finely, 1.0 g (0.025 mol) powdered NaOH and 12 cm³ butanone were added under nitrogen, and the resulting slurry was stirred vigorously for 2 hours at 60° C. The reaction mixture was allowed to cool and settle, was filtered, and the solvent removed from the filtrate to give an amber coloured resinous product.

Example 4 (TGDMQF, II, n=0, $R^1$=$R^2$=$R^3$=$R^7$=H, $R^4$=$R^8$=$CH_3$) was synthesised to study the effect of methyl substitution of the heterocyclic ring. The resin produced had a very high viscosity and could only be converted to a cured film by blending with a lower viscosity resin. The synthesis given above can be used to produce both the dimethyl ($R^4$=$R^8$=$CH_3$) and methyl ($R^4$=$CH_3$, $R^8$=H) substituted versions of the basic resin (II) with n=0. However, it has also been shown that by using substituted forms of acrylic acid, such as methacrylic acid, in the synthetic route to Example 2 (TGBDZF), certain substituted versions of (II) with n=1 are obtainable.

Examples 5 and 6 are produced by the cross-coupling reaction between the precursor compound (I) (n=0 and $R^3$ to $R^6$=H) and the known precursors of (V) (X=Cl, Y=H) and (V) (X=Y=Cl). As indicated previously, the cross-coupling reaction can be used for any combination of precursors and can also be performed with benzaldehyde. In practice, however, the Examples given here are the most promising.

In Table 1 below properties are given for the exemplified resins, and also for 50/50 physical blends by weight of (II) (n=0 and $R^1$ to $R^8$=H) with TGDDM and some halogenated TGDDM derivatives. Table 2 shows properties of unidirectional carbon fibre composites prepared from the resin/hardener combinations shown. The water absorption and wet ILSS results are after 150 days at 70° C., 83% RH. The oxidatively aged results are after 80 days at 150° C. in air.

TABLE 1

| Resin | Formula | Cured Properties using DDS | | Cured Properties using HPT1062 | |
|---|---|---|---|---|---|
| | | $T_g$ (°C.) | Water abs. | $T_g$ (°C.) | Water abs. |
| TGQF | (II), n = 0 | 298 | 7.1 | 305 | 4.8 |
| | $R^1$ to $R^8$ = H | 302,304 | | | |
| TGBDZF | (II), n = 1 | 261 | | | |
| | $R^1$ to $R^8$ = H | | | | |
| TGQB | (II), n = 0 | 270 | 5.7 | | |
| | $R^1$ = $C_6H_5$ | 272 | 6.0 | | |
| | $R^2$ to $R^8$ = H | | | | |
| TGDMQF | (II), n = 0 | Blend with GT1: | | | |
| | $R^1$ = $R^2$ = H | 272,273 | 4.9 | | |
| | $R^3$ = $R^7$ = H | | | | |
| | $R^4$ = $R^8$ = $CH_3$ | | | | |
| XC | (V), n = 0 | 290 | 5.4 | 276 | 4.2 |
| | $R^1$ to $R^8$ = H | 291 | 5.5 | | |
| | X = Cl, Y = H | | | | |
| XCD | (V), n = 0 | | | | |
| | $R^1$ to $R^8$ = H | 295 | 6.0 | | |
| | X = Y = Cl | | | | |
| Blend TGQF/ GT1 | TGQF as above. GT1 = V X = Cl, Y = H | 283 | 5.3 | 280 272 | 4.3 4.0 |
| Blend TGQF/ GT2 | TGQF as above. GT2 = V X = Br, Y = H | 278 | 5.1 | | |
| Blend TGQF/ GT3 | TGQF as above. GT3 = V X = Y = Cl | 275 270 | 5.4 5.3 | | |
| Blend TGQF/ MY720 | TGQF as above. MY720 = IV X = Y = H | 270 | 6.8 | 267 | 4.3 |

TABLE 2

| Resin | $T_g$ (°C.) | Dry ILSS (MPa) | | Water abs. (%) | Wet ILSS (MPa) | | Oxidatively aged ILSS (MPa) | |
|---|---|---|---|---|---|---|---|---|
| | | 120° C. | 150° C. | | 120° C. | 150° C. | 120° C. | 150° C. |
| TGQF/ GT1/ HPT1062 | 248 | 71 | 61 | 0.96 | 48 | 39 | — | — |
| TGQF/ DDS | 294 | — | 72 | | — | | — | 76 |
| XC/ DDS | 291 | 82 | 76 | 1.68 | 51 | 43 | 87 | 80 |
| XCD/ DDS | 287 | 82 | 75 | 1.62 | 54 | 46 | 86 | 82 |

Results for carbon fibre composite specimens

We claim:

1. A high temperature multi-functional epoxy resin precursor of formula (I):

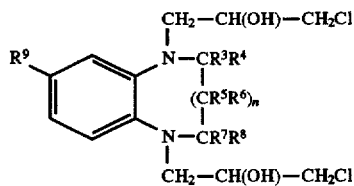

wherein $R^3$ to $R^8$ inclusive are independently selected from hydrogen, $C_1$ to $C_3$ alkyl or halo-alkyl, or aryl and wherein n=0,1 or 2, and wherein $R^9$=hydrogen, alkyl or halogen.

2. An epoxy resin wherein the precursor as claimed in claim 1 (I) is substituted at the $R^9$ position with hydrogen and self-coupled under acidic conditions in the presence of formaldehyde or benzaldehyde to give, after subsequent dehydrochlorination, a multi-functional compound of formula (II):

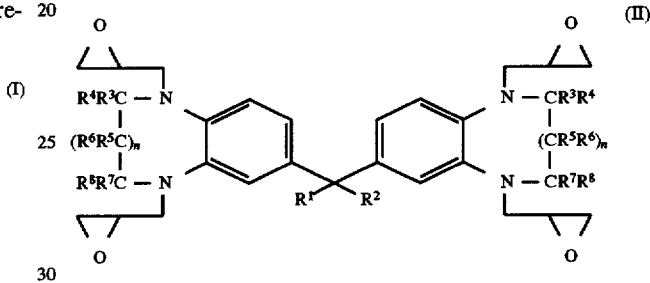

and higher oligomers (III), wherein $R^1$ to $R^8$ inclusive are independently selected from H, $C_1$ to $C_3$ alkyl, halo-alkyl, or aryl, and wherein n=0, 1 or 2 and x=0 to 10.

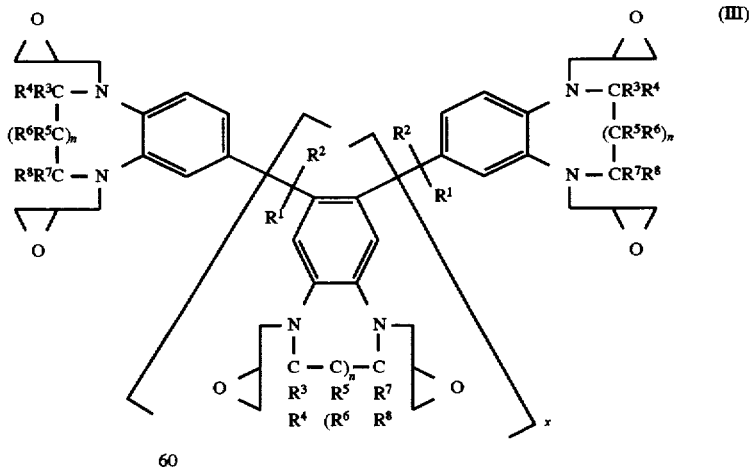

3. An epoxy resin as claimed in claim 2 wherein n=0 and $R^1$ to $R^8$ inclusive are hydrogen.

4. An epoxy resin as claimed in claim 2 wherein n=1 and $R^1$ to $R^8$ inclusive are hydrogen.

5. An epoxy resin as claimed in claim 2 wherein n=0, $R^1=C_6H_5$ and $R^2$ to $R^8$ inclusive are hydrogen.

6. An epoxy resin wherein the precursor as claimed in claim 1 (I) is substituted at the $R^9$ position with alkyl or halogen and self-coupled in the presence of formaldehyde or benzaldehyde to give, after subsequent dehydrochlorination, a multi-functional compound of formula (IV):

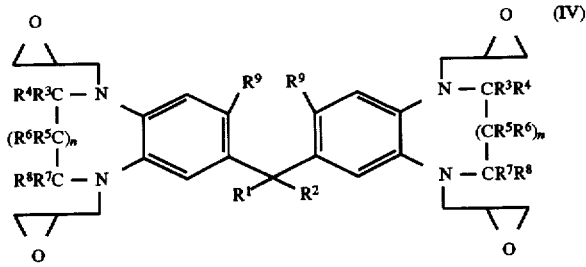

(IV)

wherein $R^1$ to $R^8$ inclusive are independently selected from hydrogen, $C_1$ to $C_3$ alkyl or halo-alkyl, or aryl, and wherein n=0, 1 or 2.

7. An epoxy resin as claimed in claim 6 wherein $R^1$ to $R^8$ are hydrogen and n=0.

8. An epoxy resin wherein the precursor as claimed in claim 1 (I) in which $R^9$ is hydrogen is cross-coupled with further precursor (I) in which $R^9$ is alkyl or halogen.

9. An epoxy resin as claimed in claim 8 wherein $R^3$ to $R^8$ are hydrogen, n=0 and $R^9$ is hydrogen or $CH_3$.

10. An epoxy resin wherein the precursor as claimed in claim 1 is cross-coupled with a precursor (V) of the formula:

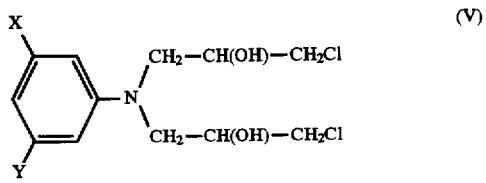

(V)

in which X and Y are independently selected from halogen, haloalkyl or hydrogen, and at least one of the groups X or Y attached to each aromatic ring is a halogen or haloalkyl.

11. An epoxy resin as claimed in claim 10 or wherein $R^3$ to $R^8$ inclusive are independently selected from hydrogen, $C_1$ to $C_3$ alkyl, halo-alkyl, or aryl, wherein n=0, 1 or 2 and wherein $R^9$ is hydrogen.

12. An epoxy resin as claimed in claim 11 wherein n=0 and $R^3$ to $R^8$ inclusive are hydrogen.

13. An epoxy resin as claimed in claim 11 wherein n=1 and $R^3$ to $R^8$ inclusive are hydrogen.

14. An epoxy resin as claimed in claim 6 wherein n=0, $R^1=C_6H_5$ and $R^2$ to $R^8$ inclusive are hydrogen.

15. An epoxy resin as claimed in claim 10 wherein n=0, $R^3$ to $R^8$ inclusive are hydrogen and $R^9$ is alkyl or halogen.

* * * * *